United States Patent
Ekre et al.

[11] Patent Number: 5,472,953
[45] Date of Patent: Dec. 5, 1995

[54] FRACTIONATED HEPARIN FOR THE THERAPEUTIC TREATMENT OF MALARIA

[76] Inventors: Hans-Peter Ekre, Pettersbergvagen 94, S-126 57 Hagersten; Johan Carlson, Marialund, S-755 97 Uppsala; Asli A. Kulane, Forskarbacken 21/420, S-104 05 Stockholm; Peter Perlmann, Malartorget 13, S-11 27 Stockholm; Mats Wahlgren, Stockbyvagen 3A, S-182 74 Stocksund; Birgitta Wahlin, Birkavagen 12, S-131 40 Nacka, all of Sweden

[21] Appl. No.: 39,205
[22] PCT Filed: Oct. 4, 1991
[86] PCT No.: PCT/SE91/00668
  § 371 Date: Jul. 28, 1993
  § 102(e) Date: Jul. 28, 1993
[87] PCT Pub. No.: WO92/05790
  PCT Pub. Date: Apr. 16, 1992

[30] Foreign Application Priority Data

Oct. 4, 1990 [SE] Sweden .................................. 9003181

[51] Int. Cl.$^6$ .......................... A61K 31/725; C08B 37/10
[52] U.S. Cl. ................................................ 514/56; 536/21
[58] Field of Search ................................ 514/56; 536/21

[56] References Cited

FOREIGN PATENT DOCUMENTS 20058397  8/1982  European Pat. Off. .

OTHER PUBLICATIONS

Dialog Information Services, File 73: EMBASE (ExcerpTa Medica) 1974–1992, Dialog accession No. 78220969, Blumenthal J et al: "Fatal malaria tropic with consumption coagulpathy", Med.Welt (Germany, West), 1977, 28/43 (1769–1771).

Andersson, L.—O, T. W. Barrowcliffe, E. Holmer, E. A. Johnsson, G. E. C. Sims. 1976 Anticoagulant properties of heparin fractioned by affinity chromatography on matrix–bound antithrombin III and by gel filtration. Thumb. Res., 9: 575–583.

Butcher, G. A., C. R. Parish, W. B. Cowdent. 1988. Inhibition of grown in vitro or *Plasmodium falciparum* by complex polysaccharides. Trans. Roy. Soc. Trop. Med. Hyg. 82: 558–559.

Cappai, R., M. R. van Schravendijte, R. Anders, M. Gregory Peterson, L. M. Thomas, A. F. Cowman, D. J. Kemp. 1989. Expression of the RESA gene in *Plasmodium falciparum* isolate FCR3 is prevented by a subtelomeric deletion. Molec. Cell Biol. 9: 3584–3587.

Carlson, J., G. Holmquist, D. W. Taylor, P. Perlmann, M. Wahlgren. 1990, Antibodies to a histidine–rich protein (Pf HRPI) disrupt spontaneous formed *plasmodium falciparum* erythrocyte rosettes. Proc. Natl. Acad. Sci. USA. 87: 2511–2515.

Danishefsky, I., H. B. Eiber, J. J. Carr. 1960. Investigations on the Chemistry of heparin. I. Desulfation and acetylation. Arch. Biochem. Biophys. 90: 114–121.

Dennis. L. H., M. E. Conrad. 1968. Anticoagulant and antimalarial action of heparin in simian malaria. Lancet 769–771.

Dejana, E., A. Callioni, A. Quintana, G. Faetano. 1979 Thromb. Res. 15:191–197.

Ekre, H–P. 1985. Inhibition of human guinea pig complement by heparin fractions differing in affinity for anti–thrombin III or in average molecular weight. Int. J. Immunopharmac. 7: 271–280.

(List continued on next page.)

*Primary Examiner*—Douglas W. Robinson
*Assistant Examiner*—Kathleen Kahler Fonda
*Attorney, Agent, or Firm*—Stroock & Stroock & Lavan

[57] ABSTRACT

The invention relates to the use of heparin with low affinity for antithrombin III for the preparation of a medicament in the treatment of malaria. The amount of the heparin with low affinity for antithrombin III could be between 2 and 200 mg in the medicament and the anticoagulant activity is preferably ≦30 IU/mg as determined by APTT.

12 Claims, 1 Drawing Sheet

OTHER PUBLICATIONS

Ekre, H–P, B. Fjellner, Ö.Hägermark. 1986. Inhibition of complement dependent experimental inflammation in human skin by different heparin fractions. Int. J. Immunopharmac. 8: 277–286.

Howard, W. A., W. E. Collins. 1972. Heparin therapy in simian *Plasmodium Knowlesi* malaria. Lancet 738–739.

Inoue, Y. and K. Nagasawa. 1976 Selective N–desulfation of heparin with dimethyl sulfoxide containing water or methanol. Carbohydr. Res. 46: 87–95.

Mitchell, A. D. 1974. Recent experience with severe and cerebral malaria. S. Afr. Med. J. 48: 1353–4.

Munir, M., T. Husada., T. H. Rampengan, I. Mustadjab, F. H. Wulur. 1980. Heparin in the treatment of cerebral malaria. Pediatric indonesiana 20: 47–50.

Reid, H. A., P. Sucharit. 1972. Ancrod, heparin and aminocaproic acid in simian knowlesi malaria. Lancet 1110–1112.

Sivaraman, C. A., A. N. Rai. Chowhuri. 1983. Effect of heparin sodium on *in vitro* development of *Plasmodium falciparum*. Ind. Jour. of Exp. Biol. 21: 247–250.

Smitskamp, H., F. H. Wolthius. 1971. New concepts in treatment of malignant tertian malaria with cerebral involvement. Brit. Med. J. 1: 714–716.

Tager, W., J. B. Jensen. 1976. Human malaria parasites in continuous culture. Science 193: 673–675.

Udomsangpetch, R., B. Wahlin, J. Carlson, K. Berzins, M. Torii, M. Aikawa, P. Perlmann, M. Wahlgren. M. 1989. *Plasmodium falciparum* infected erythrocytes form spontaneous erythrocyte rosettes. J. Exp. Med. 169: 1835–1840.

Wahlgren, M., J. Carlson, R. Udomsangpetch, P. Perlmann. 1989. Why do *Plasmodium falciparum* infected erythrocytes form spontaneous erythrocyte rosettes? Parasit. Today 5: 183–185.

Wahlin, B., M. Wahlgren, H. Perlmann, K. Berzins, A. Björkman, M. Patarroyo, P. Perlmann. 1984. Human antibodies to a M 155,000 *Plasmodium falciparum* antigen efficiently inhibit merozoite invastion. Proc. Natl. Acad. Sci. 81: 7912–791.

Jaques L. B. 1979. Heparin: An old drug with a new paradigm. Science 206: 528–533.

Sigma Chemical Company Catalog, 1989, p. 691.

FRACTIONATED HEPARIN FOR THE THERAPEUTIC TREATMENT OF MALARIA

This invention relates to the use of heparin with low affinity for antithrombin III for the preparation of a medicament in the treatment of malaria.

BACKGROUND

Heparin is best known as an inhibitor of the blood coagulation system and is thus widely used as an anticoagulant but has a number of other biological activities (Jaques 1979). It is a heterogeneous mixture of related molecules that can be fractioned according to size or affinity for antithrombin (Andersson et al 1976). Such heparin fractions vary considerably in their anticoagulant activity (Andersson et al 1976), which is dependent on antithrombin binding.

Heparin has been used for treatment of patients with *Plasmodium falciparum* malaria (Mitchell 1974; Munir et al 1980; Smitskamp and Wolthius 1971), with ambiguous results. In studies of Rhesus monkeys infected with *Plasmodium knowlesi*, treatment with heparin has, according to some authors (Dennis and Conrad 1968), efficiently cured the monkeys, while others have found it to be inefficient (Howard and Collins 1972; Reid and Sucharit 1972). In vitro heparin has been shown to inhibit invasion and development of *P. falciparum* (Butcher et al 1988; Sivaraman and Chowdhuri 1983) and in one of these studies the 50% inhibitory dose of heparin and of heparin fractions with high or low affinity for antithrombin III were reported to be the same; 1 mg/ml (Butcher et al 1988).

DESCRIPTION OF THE INVENTION

In order to further study the effect of heparin on the malaria parasite we have used different *P. falciparum* strains to analyse the invasion inhibition capacity in vitro of heparin and various heparin fractions differing in affinity for antithrombin III or in average molecular weight. We have also analysed the ability of the different heparin fractions to disrupt spontaneously formed *P. falciparum* erythrocyte rosettes, a phenomenon thought to be involved in the pathogenesis of cerebral malaria. Our studied heparin fraction include: HA-heparin, heparin with high affinity for AT III LA-heparin, heparin with low affinity for AT III HMW-heparin, high molecular weight heparin LMW-heparin, low molecular weight heparin N-acetylated HM heparin, high molecular weight heparin with low anticoagulant activity.

The invention relates to the use of heparin with low affinity for antithrombin III, LA-heparin, for the preparation of a medicament in the treatment of malaria. More specific the therapeutic dose of the heparin with low affinity for antithrombin III is between 2 and 200 mg in the medicament. The heparin with low affinity for antithrombin III has preferably a reduced bleeding time prolongation in comparision with heparin. The specific anticoagulant activity of the used LA-heparin is preferably ≦30 IU/mg as determined by APTT. A daily dose could be 0.05–5 mg per kg. The heparin with low affinity for antithrombin III could be used in combination with other medicaments for the treatment of malaria.

The invention also covers a method for the treatment of malaria, wherein a therapeutically effective amount of heparin with low affinity for antithrombin III is administered to a patient in need of such treatment.

It is preferred that the administration is made by injection or infusion. A suitable effective amount of the heparin is such as to result in a daily dose of from about 2 to about 200 mg.

The medicament for the treatment of malaria prepared in accordance with the present invention may thus be formulated in accordance with traditional pharmaceutical practice for use for therapeutic purposes. Such compositions may include the active ingredient heparin with low affinity for antithrombin III, in combination with a pharmaceutically acceptable carrier, which may be solid, semisolid or liquid. The compositions constituting such medicament may be designed for administration through different routes.

Suitable forms of the composition used in applying the techniques of the present invention include tablets, capsules, syrups, suspensions, solutions and forms suitable for injection or infusion. The latter forms intended for injection or infusion are preferred. Such compositions may contain conventional pharmaceutically acceptable materials, such as diluents, binders, colours, flavours, preservatives, disintegrates and the like in accordance with conventional pharmaceutical practice in a manner well understood by those skilled in the art of formulating drugs.

Injectable or infusable compositions of the heparin are particularly suitable as levels of heparin and can occur after administration by injection or infusion resulting in effective treatment of malaria.

The administered dose of the active ingredient, i.e. heparin with low affinity for antithrombin III, may vary between broad limits, but a preferred range may be between about 2 and about 200 mg per day. The dose is, of course, dependent on the degree and type of malaria, type and condition of the patient and will be determined from case to case.

Tables 1–4 refer to the studies shown in examples 1–5.

Figure 1:
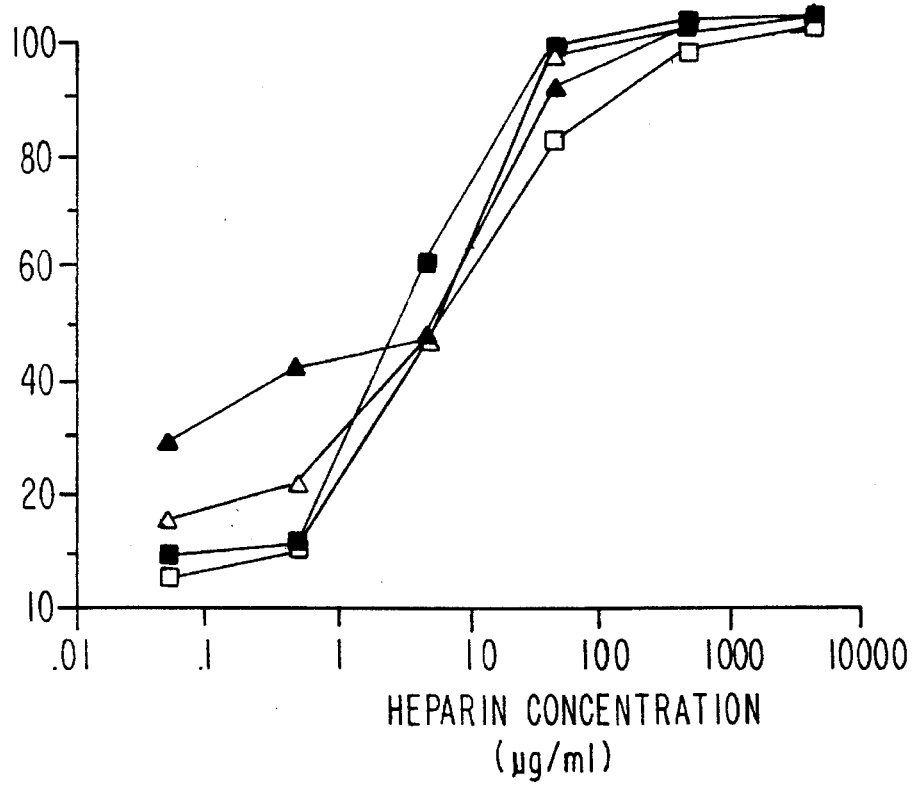
FIG. 1 shows Merozoite invasion inhibition of different strains of *P. falciparum*.

The following materials and methods have been used.

Heparin

Varying concentrations of standard sodium heparin (0.05–5,000 µg/ml) without preservatives (Lövens, AB, Malmö, Sweden) were tested on four *P. falciparum* strains for their effect on merozoite invasion. In this context, 10 µg standard heparin/ml corresponds to approximately 1 U/ml.

Fractionation of pharmaceutical grade sodium heparin (Kabi) was carried out by gel filtration on Sephacryl S-200 (Pharmacia) to yield fractions of high and low average molecular weight (MW), and by affinity chromatography on antithrombin-Sepharose 4B for preparation of fractions with high (HA) and low (LA) affinity for antithrombin III (AT III), as described previously (Andersson et al 1976; Ekre 1985; Ekre et al 1986). A high MW fraction with low antithrombin affinity was prepared by N-desulphation (Inoue and Nagasawa 1976) and N-acetylation (Danishefsky et al 1960) of a high MW fraction.

Anticoagulant activities were determined in an APTT (activated partial thromboplastin time) assay (Andersson et al 1976) and expressed in international units using as a reference the 3rd International Standard for Heparin from the National Institute for Biological Standards and Control, London, U.K. The characteristics of the heparin fractions are summarized in Table 1.

The heparin fractions were compared with the standard heparin from which they were derived at varying concentrations as indicated.

Preparation of LA-Heparin

Antithrombin III, purified from human plasma by Kabi Biopharma, was coupled to CNBr-activated Sepharose 4B (Pharmacia) at a density of ca 5 mg antithrombin/ml gel. Five hundred ml of this gel, packed in a 5 cm×30 cm column, was equilibrated in 0.05M Tris buffer, pH 7.4, with 0.15M NaCl. For preparation of LA-heparin approximately 300 mg of heparin, dissolved in equilibration buffer, was applied to the column and the unadsorbed heparin collected.

For preparation of HA-heparin a heparin load of 600–900 mg was applied to the column. After washing of the column the HA-heparin was desorbed by increasing the NaCl concentration to 1.5M.

LA-heparin prepared using this or similar technology has a low anticoagulant activity. The magnitude of this activity varies depending on the assay and the technique applied, but using an APTT and an international standard, LA-heparin typically has an anticoagulant activity of ≦30 IU/mg.

Bleeding Time

To compare the haemorragic effect of heparin and LA-heparin a template bleeding time test was performed in Spraque-Dawley rate (Dejana et al 1979). Animals weighing 200–250 g were anesthetised with Mebumal/Stesolid (Dumex A/S, Copenhagen). The template device (Simplate, General Diagnostics, Durham, N.C.) was applied longitudinally to the dorsal part of the tail, taking care to avoid large veins. Blood from the wound was then carefully removed every 30 seconds with blotting paper. A minimum of five rats were used for each compound and dose. Bleeding times were measured from the moment the tail was incised until the first arrest of bleeding. The bleeding time was recorded with an accuracy of 30 seconds and bleeding times longer than 20 minutes were noted as >20. Two bleeding times were always determined in each rat, i.e. 10 minutes before and 10 minutes after drug administration, and the results expressed as the prolongation of bleeding time.

Parasites

Parasites from four different strains of *Plasmodium falciparum* were cultivated in vitro in erythrocytes of blood group O+ according to the method of Trager and Jansen (1976). These strains included F32 (Tanzania); FCR-3 K+ (Gambia); a cloned variant of FCR-3 lacking the PF155/RESA antigen (Cappai et al 1989) and R+PA1 which is a cloned rosetting parasite obtained from the Palo Alto strain (Uganda) (Udomsangpetch et al 1989). Reinvasion inhibition by standard heparin was tested on all four strains and by the heparin fractions on strains F32 and R+PA1. Ability to disrupt erythrocyte rosettes by the heparin fractions was tested on the rosetting strain R+PA1.

Merozoite Invasion Inhibition Assay

Merozoite invasion inhibition in vitro was performed as described earlier by Wählin et al. (1984). In brief, cultures of *P. falciparum* consisting mainly of late trophozoites and early schizonts were diluted to a starting parasitaemia of approximately 0.5% and a hematocrit of 2%. Microcultures were set up in 96 well, flat bottomed, microculture plates (100 μl per well). The cultures were incubated at 37° C. for 20 hours in 100 μl complete tissue culture medium, supplemented with increasing concentrations of heparin or heparin fractions. The parasitaemia after incubation varied between 1.5–3%. After washing the cultures twice, erythrocyte monolayers were prepared on multitest slides by glutaraldehyde fixation and air drying. All tests were set up in quadruplicates. The parasites were stained for 10 seconds with acridine orange (10 μg/ml) and counted under incident ultraviolet light in a fluorescene microscope. The percentage of parasitaemia was calculated from 40 000 erythrocytes that were screened. Invasion inhibition was calculated as:

100×(% parasitaemia in control-% parasitaemia in test)/(% parasitaemia in control).

To investigate whether the effect of heparin is reversible, late stages of parasites (trophozoites and early schizonts) were incubated for 6 hours with 1, 0.1, or 0.01 mg heparin/ml. After 6 hours, half of the cells were washed twice with culture medium and then incubated for 14 more hours in medium only while the other half remained in heparin during the whole period of 20 hours.

Disruption of Erythrocyte Rosettes

A *P. falciparum* isolate (Palo Alto, Uganda; R+PA1, a cloned rosetting parasite obtained from the Palo Alto strain) was kept in continuous in vitro culture according to standard procedures with 10% normal serum added to the buffered medium. Enrichment was made on Ficoll-Isopaque (FIP) and cloning by limiting dilution. Studies were performed on cultures with 5% haematocrit, 4–5% parasitaemia at late stage and a 70–80% (R+PA1) rosetting. The parasite culture was mixed with a small amount of acridine orange, mounted on glass slides and 50 consecutive vision fields were counted with a 40× lens in incident UV light (Leitz Laborlux K microscope). Fields were counted diagonally over the slide, from one corner to the other, in order to compensate for an uneven distribution of rosettes on the glass. Infected erythrocytes that had bound two or more non-infected ones were scored as rosettes and the rosetting was expressed as the number of infected erythrocytes in rosettes relative to the total number of late stage (trophozoite and schizont) infected erythrocytes. Aliquots (25–50 μl) of the cloned parasite R+PA1 were mixed with various dilutions of normal heparin and the different heparin fractions and incubated in a 96-well microtiter plate, covered with parafilm and lid, (Linbro, Flow Labs., Rockville, Md. U.S.A.) at 37° C. for 30 minutes prior to assessment of rosetting. The rosetting of each well was compared to that of a control with normal serum as additive.

EXAMPLE 1

Effect of Standard Heparin on the Inhibition of Invasion of Different Strains of *P. falciparum*

The effect of standard heparin on the inhibition of invasion of different strains of *P. falciparum* is presented in FIG. 1. The figure shows merozoite invasion inhibition of different strains of *P. falciparum* R+PA1 (■), F32 (□), FCR3K+ (▲) and FCR3 PF155(−) (▲) by various concentrations of heparin μg/ml (abscissa). The percentage of invasion inhibition (ordinate) was obtained after 20 hours of incubation. The invasion of merozoites into RBC was totally inhibited in all tested strains when high concentrations of heparin (≧100 μg/ml) were used. At concentrations of 5–10 μg/ml of heparin, 50% invasion inhibition was seen with all strains.

EXAMPLE 2

Effect on Merozoite Invasion on Two P. falciparum Strains

Different fractions of heparin, separated by molecular weight or affinity for antithrombin III, were tested for their effect on merozoite invasion on two P. falciparum strains. As shown in Table 2 (strain F32), the low MW fraction was the least effective of all fractions, with a 50% invasion inhibition concentration of 70 µg/ml. The high MW fractions and the one with high affinity for AT III were more or less as active as the standard heparin, with 50% invasion inhibition concentrations of about 10 µg/ml. The most efficient fraction for inhibition was the low affinity fraction which lacks anticoagulant properties. This fraction had a 50% invasion inhibition concentration of 1 µg/ml (Table 2). The results were the same for the R$^+$PA1 strain (data not shown).

A fraction of heparin combining high MW and low anticoagulant activity (achieved by N-acetylation) was also tested for the effect on invasion. As seen in Table 2, this fraction had the same 50% invasion inhibition concentration as the high MW fraction, 10 and 11 µg/ml respectively.

EXAMPLE 3

The Reversible Effect of Standard Heparin

As seen in Table 3, the effect of standard heparin (Kabi) was reversible at all concentrations tested. The percentage of parasitaemia was the same in cultures exposed to heparin (1000 µg/ml) for six hours and then washed as in the heparin free controls, 1.9% and 1.8% respectively, while cultures treated with heparin (1000 µg/ml) for 20 hours had no parasitaemia (=100% inhibition).

EXAMPLE 4

Figure 2:
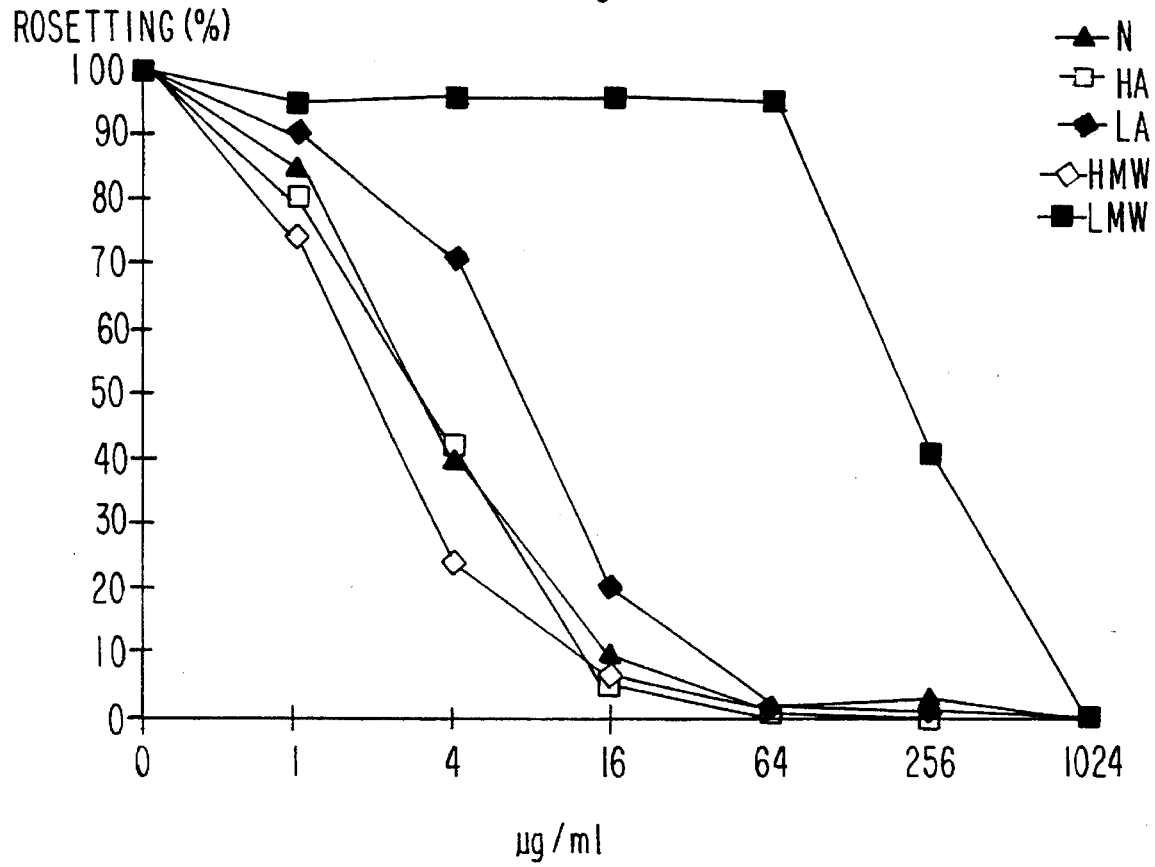
FIG. 2 shows disrupting effect of normal heparin and heparin fractions on the rosetting.

The Effect of Heparin and the Heparin Fractions on Disruption of Erythrocyte Rosettes The effect of heparin and the heparin fractions on disruption of erythrocyte rosettes is shown in FIG. 2. The figure shows the disrupting effect of normal heparin (N) and heparin fractions on the rosetting. (HA=high affinity; LA=low affinity; HMW=high MW; LMW=low MW). The potency of the different fractions is very similar except for the low MW fraction which is about 50 times less potent as compared to heparin and the other fractions. Thus, disruption of erythrocyte rosettes or prevention of erythrocyte rosette formation by heparin is independent of its anticoagulant activity but requires heparin molecules with an average MW of >5.600 daltons.

EXAMPLE 5

Bleeding Times for Heparin and the LA-Heparin

The bleeding times for heparin and the LA-heparin are shown in Table 4. Standard heparin at 2 mg/kg resulted in a bleeding time exceeding 20 minutes in all rats tested and at 1 mg/kg it prolonged the bleeding time by 4.5 minutes. In contrast, an eight times higher dose of LA-heparin, 8 mg/kg, was required to get a significant prolongation of the bleeding time, 4.2 minutes. Thus, the ability to affect bleeding is markedly reduced for LA-heparin as compared to standard heparin.

DISCUSSION

We have shown that heparin may be a more potent drug for inhibition of merozoite invasion in vitro than was previously known. No differences between the four different P. falciparum strains tested were found, all requiring approximately 5 µg/ml of heparin for 50% invasion inhibition. In earlier studies of merozoite invasion inhibition in vitro with heparin (Butcher et al 1988; Sivaraman and Chowdhuri 1983), 15–50 times more heparin was needed to achieve 50% invasion inhibition. The concentration of heparin found by us to be active is within the range used for in vivo treatment of humans for e.g. thrombosis prophylaxis and deep vein thrombosis therapy.

Heparin fractions differing in molecular weight or affinity for AT III were all efficient inhibitors of invasion. The most potent fraction was the one with low affinity for AT III. This fraction was almost 10 times more efficient than ordinary heparin or than the high affinity fraction. These findings are new and surprising since Butcher et al (1988) found that the inhibitory effect of high and low affinity heparin fractions did not differ. Butcher et al used a concentration of 1 mg/ml in their studies, a concentration which is 1000 times higher than the concentration of LA-heparin found to be active in our studies (1 µg/mg).

Apparently, anticoagulant properties or antithrombin III affinity are not essential for parasite inhibition. The low risk for bleeding (Table 4) and the high parasite invasion inhibition potency (Table 2) associated with LA-heparin, as shown here, makes LA-heparin a potential medicament in malaria, where the risk for bleeding prevents the use of normal heparin.

The high MW fraction was as effective as normal heparin and almost 10 times more effecient than the low MW fraction, indicating that the most active components of heparin are of relatively high MW. The N-acetylated high MW fraction, lacking anticoagulant activity, was as potent as the non-modified high MW fraction, again indicating that inhibition of invasion and of blood coagulation are separate properties of heparin. This modified fraction had lower invasion inhibition potency than the low affinity heparin suggesting that low anticoagulant activity combined with intact N-sulfation and/or "normal" size distribution is required for higher potency. It is possible that a high MW fraction depleted of material with high affinity for antithrombin would be equally or even more potent than the low affinity heparin fraction. Comparisons including a high MW low affinity heparin and N-acetylated standard heparin should resolve this question. The reason why the low affinity heparin fraction was the most efficient inhibitor in these experiments is presently unknown.

The mode of action of heparin on parasite invasion is not known. Heparin seems to have no permanent effect on the intra erythrocytic parasites, since inhibition was reversible if heparin was washed off before the schizonts were bursting. In contrast to Butcher et al (1988), no preventive effect of heparin on the bursting of schizonts and release of merozoites was found. Even at high concentrations of heparin, all schizonts bursted and no parasites were detected in the cultures. However, whether heparin is acting on free merozoites after their release or binds to the membrane of uninfected erythrocytes and thus blocks the penetration of the merozoite into the cell is not known. Further experiments are needed to study this mechanism.

Heparin has also been shown to exhibit a strong and dose dependant capacity on another mechanism implied to be involved in the pathogenesis of severe malaria, namely to revert spontaneous erythrocyte rosetting in *P. faciparum* malaria (Carlson et al 1990; Udomsangpetch et al 1989). This rosetting phenomenon has been proposed to be involved in parasite sequestration as well as in merozoite invasion and in the pathology of severe malaria (Carlson et al 1990; Wahlgren et al 1989). Thus, in addition to its effect on parasite invasion into the erythrocyte, heparin may also have a beneficial effect on the clinical outcome of, or the prevention of, cerebral malaria by dissolving, or preventing formation of, aggregates of infected and uninfected red blood cells in the patients' vessels. A new finding shown here is that the heparin fraction which has low anticoagulant and low bleeding-inducing effects, and which is the most efficient merozoite invasion inhibitor, is as efficient in reversing rosette formation as normal heparin (FIG. 2). Since the small bleeding risk associated with the therapeutic use of heparin is increased in malaria patients due to the disturbed haemostasis, heparin fractions with low anticoagulant activity and low potency in bleeding time prolongation should be of potential therapeutic value for treatment of malaria.

From our findings we can thus state that low affinity heparin (LA-heparin) has a very good effect, at low concentrations, on malaria in vitro. This LA-heparin has been prepared by removing heparin with high affinity for anti-thrombin III from normal heparin, has a low anticoagulant activity ($\leq 30$ IU/mg in APTT) and a marked lower bleeding risk than heparin. These findings are surprising and new and have never been disclosed or expected before. The use of LA-heparin in the preparation of a medicament for the treatment of malaria is of therapeutic value. LA-heparin may be used alone or in combination with established or new medicaments for the treatment of malaria. LA-heparin may be especially useful if the malaria is caused by parasites resistant to the chemotherapic agents established for treatment of malaria.

REFERENCES

Anderson, L.-O., T. W. Barrowcliffe, E. Holmer, E. A. Johnsson, G. E. C. Sims. 1976 Anticoagulant properties of heparin fractioned by affinity chromatography on matrix-bound antithrombin III and by gel filtration. Thromb. Res., 9: 575–583.

Butcher, G. A., C. R. Parish., W. B. Cowdent. 1988. Inhibition of growth in vitro of *Plasmodium falciparum* by complex polysaccharides. Trans. Roy. Soc. Trop. Med. Hyg. 82: 558–559.

Cappai, R., M. R. van Schravendijte, R. Anders, M. Gregory Peterson, L. M. Thomas, A. F. Cowman, D. J. Kemp. 1989. Expression of the RESA gene in *Plasmodium falciparum* isolate FCR3 is prevented by a subtelomeric deletion. Molec. Cell Biol. 9: 3584–3587.

Carlson, J., G. Holmquist, D. W. Taylor, P. Perlmann, M. Wahlgren. 1990, Antibodies to a histidine-rich protein (Pf HRPI) disrupt spontaneous formed *Plasmodium falciparum* erythrocyte rosettes. Proc. Natl. Acad. Sci. U.S.A. 87: 2511–2515.

Danishefsky, I., H. B. Eiber, J. J. Carr. 1960. Investigations on the chemistry of heparin. I. Desulfation and acetylation. Arch. Biochem. Biophys. 90: 114–121.

Dennis, L. H., M. E. Conrad. 1968. Anticoagulant and antimalarial action of heparin in simian malaria. Lancet 769–771.

Dejana, E., A. Callioni, A. Quintana, G. Gaetano. 1979 Thromb. Res. 15: 191–197.

Ekre, H-P. 1985. Inhibition of human guinea pig complement by heparin fractions differing in affinity for anti-thrombin III or in average molecular weight. Int. J. Immunopharmac. 7: 271–280.

Ekre, H.-P., B. Fjellner, Ö. Hägermark. 1986. Inhibition of complement dependant experimental inflammation in human skin by different heparin fractions. Int. J. Immunopharmac. 8: 277–286.

Howard, W. A., W. E. Collins. 1972. Heparin therapy in simian *Plasmodium knowlesi* malaria. Lancet 738–739.

Inoue, Y. and K. Nagasawa. 1976 Selective N-desulfation of heparin with dimethyl sulfoxide containing water or methanol. Carbohydr. Res. 46: 87–95.

Jaques L. B. 1979. Heparin: An old drug with a new paradigm. Science 206: 528–533.

Mitchell, A. D. 1974. Recent experience with severe and cerebral malaria. S. Afr. Med. J. 48: 1353–4.

Munir, M., T. Husada., T. H. Rampengan, I. Mustadjab, F. H. Wulur. 1980. Heparin in the treatment of cerebral malaria. Pediatric Indonesiana 20: 47–50.

Reid, H. A., P. Sucharit. 1972. Ancrod, heparin and aminocaproic acid in simian knowlesi malaria. Lancet 1110–1112.

Sivaraman, C. A., A. N. Rai. Chowdhuri. 1983. Effect of heparin sodium on in vitro development of *Plasmodium falciparum*. Ind. Jour. of Exp. Biol. 21: 247–250.

Smitskamp, H., F. H. Wolthius. 1971. New concepts in treatment of malignant tertian malaria with cerebral involvement. Brit. Med. J. 1: 714–716.

Tager, W., J. B. Jensen. 1976. Human malaria parasites in continuous culture. Science 193: 673–675.

Udomsangpetch, R., B. Wåhlin, J. Carlson, K. Berzins, M. Torii, M. Aikawa, P. Perlmann, M. Wahlgren. M. 1989. *Plasmodium falciparum* infected erythrocytes form spontaneous erythrocyte rosettes. J. Exp. Med. 169: 1835–1840.

Wahlgren, M., J. Carlson, R. Udomsangpetch, P. Perlmann. 1989. Why do *Plasmodium falciparum* infected erythrocytes form spontaneous erythrocyte rosettes? Parasit. Today 5: 183–185.

Wåhlin, B., M. Wahlgren, H. Perlmann, K. Berzins, A. Björkman, M. Patarroyo, P. Perlmann. 1984. Human antibodies to a M 155,000 *Plasmodium falciparum* antigen efficiently inhibit merozoite invasion. Proc. Natl. Acad. Sci. 81: 7912–791.

TABLE 1

| The Characteristics of heparin fractions. | | |
|---|---|---|
| | Average MW (daltons) | Anticoagulant activity (IU/mg) |
| Heparin Kabi | 11,000 | 180 |
| HA-heparin[a] | 11,500 | 340 |
| LA-heparin[b] | 10,500 | 28 |
| HMW-heparin[c] | 17,000 | 270 |
| LMW-heparin[d] | 5,600 | 21 |
| N-acetylated HM heparin[e] | 16,000 | <10 |

[a] Heparin with high affinity for AT III
[b] Heparin with low affinity for AT III
[c] High molecular weight heparin
[d] Low molecular weight heparin
[e] High molecular weight heparin with low anticoagulant activity.

TABLE 2

Invasion inhibition of *P. falciparum* merozoites by different heparin fractions.

| Compound[a] | 50% invasion inhibition concentration μg/ml |
|---|---|
| Heparin Kabi | 9 |
| HA-heparin | 10 |
| LA-heparin | 1 |
| HMW-heparin | 11 |
| LMW-heparin | 70 |
| N-acetylated HMW-heparin | 10 |

[a]see foot of Table 1

TABLE 3

Reversibility of merozoite invasion inhibition by heparin.

| Cultures | Heparin (μg/ml) | % Parasitaemia | % Invasion Inhibition |
|---|---|---|---|
| Medium[a] | — | 1.8 | — |
| Heparin[b] | 1000 | 0 | 100 |
| Heparin | 100 | 0.3 | 83 |
| Heparin | 10 | 1.1 | 35 |
| Heparin-washed[c] | 1000 | 1.9 | 0 |
| Heparin-washed | 100 | 1.9 | 0 |
| Heparin-washed | 10 | 1.8 | 0 |

[a]Parasites incubated for 20 hours in medium (control). The parasitaemia at the beginning of the experiment was 0.6%
[b]Parasites incubated for 20 hours in the presence of heparin at various concentrations.
[c]Parasites incubated for 6 hours in the presence of heparin at various concentrations, washed in medium and then incubated for 14 hours more in medium.

TABLE 4

Bleeding time in rat tail after administration of heparin or LA-heparin.

| | | Bleeding time | |
|---|---|---|---|
| Compound | Dose mg/kg | prolongation minutes | >20 min % |
| Heparin | 1 | 4.5 | 0 |
| | 2 | 17.3 | 100 |
| LA-heparin | 4 | 1.9 | 0 |
| | 8 | 4.2 | 0 |

For details see text under Bleeding time.

We claim:

1. A method of treating malaria comprising administering to an individual in need of such treatment an effective amount of a medicament containing a heparin fraction having low affinity for antithrombin III, wherein the effective amount of the medicament comprises a daily dosage of the heparin fraction in the range between approximately 0.05 mg/kg of body weight of the individual to approximately 5 mg/kg of body weight of the individual.

2. The method of claim 1, wherein the medicament is administered by an injection.

3. The method of claim 1, wherein the medicament is administered by infusion.

4. The method of claim 1, wherein the heparin fraction has a bleeding time prolongation which is less than the bleeding time prolongation of unfractionated heparin.

5. The method of claim 1, wherein the heparin fraction has an anticoagulant activity which is $\leq 30$ IU/mg as determined by activated partial thromboplastin time assay.

6. The method of claim 1, wherein the medicament containing the heparin fraction is administered with at least one additional medicament for treating malaria.

7. A method of treating malaria comprising administering to an individual in need of such treatment an effective amount of a medicament containing a heparin fraction having low affinity for antithrombin III, wherein the effective amount of the medicament comprises a daily dosage of the heparin fraction in the range between approximately 2 mg to approximately 200 mg.

8. The method of claim 7, wherein the medicament is administered by an injection.

9. The method of claim 7, wherein the medicament is administered by infusion.

10. The method of claim 7, wherein the heparin fraction has a bleeding time prolongation which is less than the bleeding time prolongation of unfractionated heparin.

11. The method of claim 7, wherein the heparin fraction has an anticoagulant activity which is $\leq 30$ IU/mg as determined by activated partial thromboplastin time assay.

12. The method of claim 7, wherein the medicament comprising the heparin fraction is administered with at least one additional medicament for treating malaria.

* * * * *